United States Patent [19]

Djerassi

[11] 4,197,847
[45] Apr. 15, 1980

[54] METHOD AND APPARATUS FOR COLLECTING TRANSFUSABLE GRANULOCYTES

[76] Inventor: Isaac Djerassi, 2034 Delancey Pl., Philadelphia, Pa. 19103

[21] Appl. No.: 843,928

[22] Filed: Oct. 20, 1977

Related U.S. Application Data

[63] Continuation-in-part of Ser. No. 783,380, Mar. 31, 1977, Pat. No. 4,111,199.

[51] Int. Cl.² ............................................. A61M 5/00
[52] U.S. Cl. ............................. 128/214 R; 128/214 D
[58] Field of Search ............ 128/214 R, 214 D, 214.2, 128/272, DIG. 24; 233/2; 210/DIG. 23

[56] References Cited

U.S. PATENT DOCUMENTS

| 3,489,145 | 1/1970 | Judson et al. | 128/214 R |
| 4,058,363 | 11/1977 | Silbert | 128/214 D |

FOREIGN PATENT DOCUMENTS

2537128  3/1976  Fed. Rep. of Germany ...... 128/214 R

OTHER PUBLICATIONS

"A Method for Separation of Granulocytes from Normal Human Blood Using Hydroxyethyl Starch", *Preparative Biochem*, Roy et al., 1971.

"Increased Efficiency of Leukocyte Collection by the Addition of HES to the Continuous Flow Centrifuge", *Blood*, Mishler et al., vol. 44, 10-1971.

*Primary Examiner*—Robert W. Michell
*Assistant Examiner*—Thomas J. Wallen
*Attorney, Agent, or Firm*—Caesar, Rivise, Bernstein & Cohen, Ltd.

[57] ABSTRACT

In carrying out the process of this invention, there is a closed bag system comprising a first bag used for sedimenting the red cells and a second bag used for collecting the sedimented red cells. The two bags are connected by a flexible plastic transfer tube. The sedimenting bag has a second transfer tube leading thereto for introducing the packed red and white cells and the Saline solution of a sedimenting agent. A third tube is connected to the sedimenting bag for withdrawing white cells. The red cell bag has a second tube for the addition of plasma and a third tube for returning the plasma and red cells to a vein of the donor. As an optional feature, the withdrawn whole blood passes directly to an interrupted flow centrifuge which spins off the plasma and platelets, and from which the packed red and white cells are pumped to the sedimenting plastic bag.

9 Claims, 7 Drawing Figures

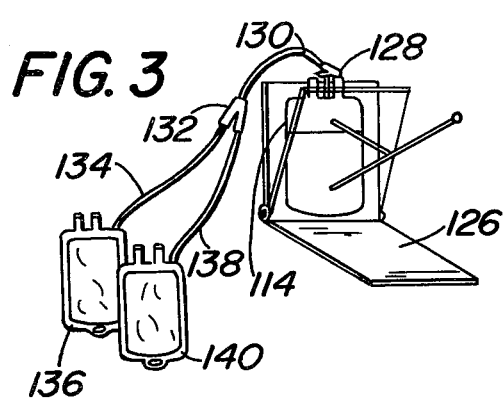
FIG. 3
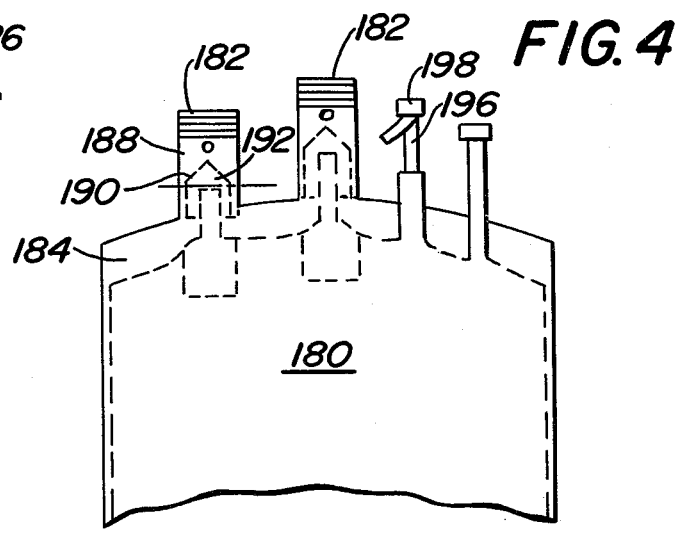
FIG. 4
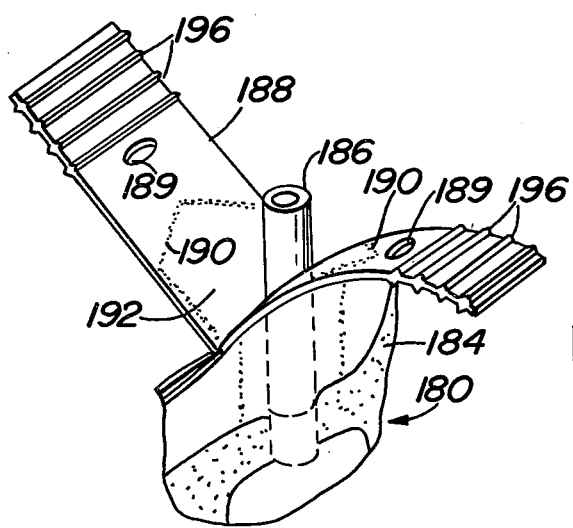
FIG. 5
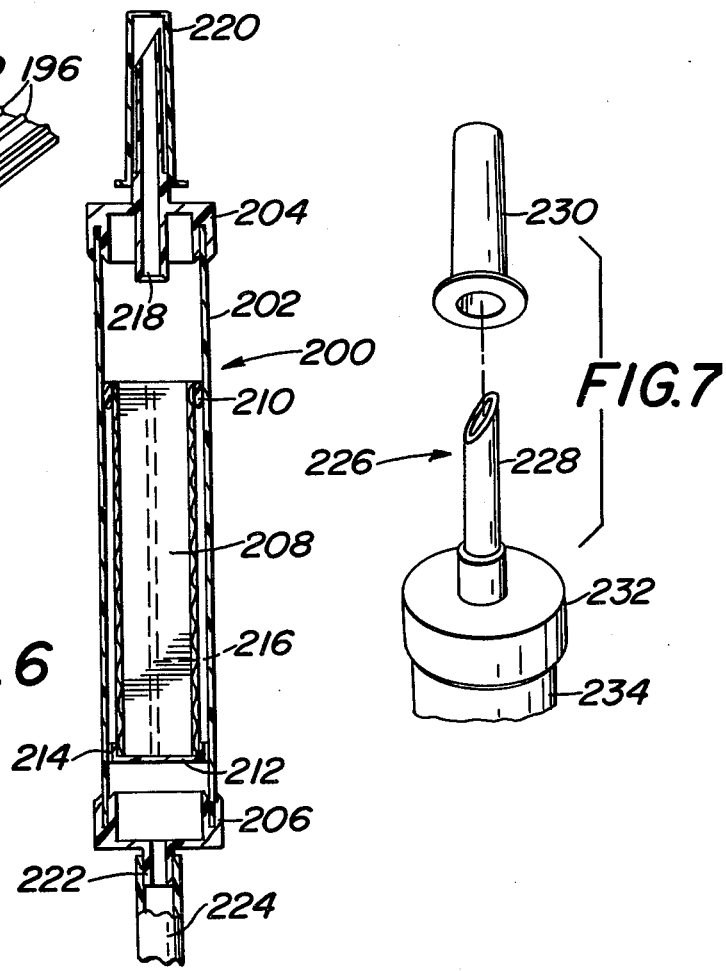
FIG. 6
FIG. 7

METHOD AND APPARATUS FOR COLLECTING TRANSFUSABLE GRANULOCYTES

This application is a continuation-in-part of my U.S. Application Ser. No. 783,380, filed Mar. 31, 1977 and entitled "Method of Collecting Transfusable Granulocytes by Gravity Leukopheresis", the disclosure of which application is incorporated by reference herein. Said application Ser. No. 783,380 issued into U.S. Pat. No. 4,111,199 on Sept. 5, 1978.

This invention relates to a method and apparatus for carrying out a leukopheresis for obtaining granulocytes for transfusion, and, more particularly, to a leukopheresis process and apparatus that utilizes gravity sedimentation to remove red cells from the white cells which are to be injected.

Human blood comprises red cells (erythrocytes) and white cells (leukocytes). The leukocytes in turn consist of monocytes, lymphocytes and granulocytes. The granulocytes comprise approximately 70% to 80% of the leukocytes. The granulocytes are involved in various defense and repair functions. They are the first cells to appear at a site of inflammation. Their function is to fight bacterial infection of a human being.

Granulocytes are now transferred into patients for various purposes. They are used where therapy with appropriate antibiotics has failed to control an infection in the granulocytopenic patient. They are used in the treatment of patients with acute or chronic leukemia, aplastic anemia or bone marrow transplant recipients.

The use of transfusions of human granulocytes to infected leukopenic patients commenced about twenty years ago. The original method of obtaining granulocytes was to remove a small quantity of blood, such as a pint (473 ml), into a plastic bag and centrifuge the bag in order to remove the plasma and platelets. The remaining red and white cells were then permitted to rest in the bag and the red cells would sediment. The white cells would remain as a buffy coat above the red cells. The red cells could then be withdrawn and the granulocytes and other white cells could be recoved from the buffy coat. These granulocytes were then injected into the donee or patient.

One of the problems with this type of separation is that a given donor could only provide small quantities of white cells in any given time period since the donor can only donate one pint (473 ml) of whole blood every eight weeks. This problem was overcome by the advent of leukopheresis. Utilizing leukopheresis, large quantities of white cells could be obtained in a given day from the donor. In the leukopheresis process, blood is continuously withdrawn from the donor, the white cells are removed from the blood and the red cells and plasma, and most of the platelets, are reinjected into the donor. In a leukopheresis process on a donor, as many as twenty-four pints (473 ml each) have been processed. This allows collection of very large numbers of granulocytes from a single donor.

Until the advent of the process described in my aforementioned Application Ser. No. 783,380, leukophereses were conducted by either continuous or interrupted flow centrifugation or by filtration leukopheresis. A description of all of these methods and the use of the recovered granulocytes can be found in a publication entitled "Leukapheresis And Granulocyte Transfusions", published by American Association of Blood Banks, Washington, D. C., in 1975. Apparatus for carrying out the continuous flow centrifugation leukopheresis can be found in U.S. Pat. Nos. 3,489,145 and 3,655,123. Apparatus for carrying out filtration leukopheresis can be found in Applicant's prior U.S. Pat. Nos. 3,802,432 and 3,892,236. Both the continuous flow centrifugation and filtration leukopheresis are based on establishing a vein-to-vein in extracorporeal blood circulation and extracting continuously the granulocytes from recirculated blood.

The efficiency of centrifugation for separating normal human granulocytes was increased by adding a high molecular weight material, namely, hydroxyethyl starch, to the blood prior to or during the centrifugation. This procedure was based on Applicant's prior discovery that this material is very effective and superior to other similar materials for separation of granulocytes from red cells by simple gravity sedimentation, unassisted by centrifugation. The ability of large molecular weight materials to facilitate the separation of white blood cells from red cells has been known for some time. High molecular weight dextran has been used for the collection of laboratory amounts of white cells for some twenty years. Among the high molecular weight materials used for these purposes were polyvinylpyrrolidone, dextran or hydroxyethyl starch (HES). The effect of these materials is based on the fact that such materials cause reversible aggregation of red cells, which then sediment faster than single granulocytes in an aqueous medium. The mechanism for this faster sedimentation is not clearly understood. However, it is believed that the large molecular weight materials cause an increase of the so-called sedimentation rate of the blood. Since the sedimentation rate of blood is also increased by natural products found in the blood, such as fibrinogen, addition of pure fibrinogen could also be used for separation of granulocytes from red cells. In fact, all large molecules, synthetic or natural, capable of increasing the sedimentation rate of blood would produce the same result.

Separation of blood into elements can therefore be achieved by simple gravity, or in other words, letting blood with an anticoagulant stand in an appropriate container without being disturbed for a period of time.

Under these conditions the red cells would settle at the bottom of the container, being the heaviest, with the white cells concentrating in the upper layers of the red cells and just above them, to form the so-called buffy coat. The plasma with the platelets floats above the red cells and the buffy coat. The separation of these elements into separate containers can be achieved by aspiration of each layer or by squeezing the original container, if flexible, and expulsing the portions of the contents as they come to a suitably located opening. The latter process is the basis for the separation of blood components using plastic bags and centrifugation. The speed of separation of the blood elements by gravity is not practicable for pheresis procedures because of the many hours required for sedimentation of the elements in whole blood and an anticoagulant (ACD), without additives.

Such separation is greatly increased by the addition to the blood of materials which increase the sedimentation rate, such as high molecular weight dextran, HES, fibrinogen, polyvinylpyrrolidone, and many other materials generally referred to as plasma expanders or red blood cell sedimenting agents.

The addition of such materials, and particularly HES, is necessary for efficient separation of granulocytes from the red cells of human blood, even when the blood is centrifuged. By adding HES to the donor's blood the efficiency of the continuous flow centrifuges or the discontinuous flow centrifuges has been increased from 5% to about 20% and 40%, respectively. The use of HES in fact made these centrifuges more practical, even though not ideal, for harvesting normal human granulocytes for transfusion.

Up until the advent of the invention disclosed and claimed in my aforementioned U.S. Application Ser. No. 783,380, as pointed out above, collection of human granulocytes in amounts suitable for transfusion has been accomplished only by methods of pheresis with centrifugation, with or without HES or other high molecular weight materials, or by filtration. Prior to my aforementioned invention, sedimentation unassisted by centrifugation for the separation of white cells had not been used for collection of granulocytes to be transfused, nor had it been used in a pheresis process.

The process disclosed and claimed in my aforementioned U.S. Application Ser. No. 783,380 comprises withdrawing a portion of blood from a human, separating the red and white cells from the plasma and platelets in the blood and mixing the packed red and white cells with a solution comprising a blood cell sedimenting agent and an isotonic balanced salt solution, such as Normal Saline. The red blood cell sedimenting agent was present in a range of about 1½% to 6% by weight of the salt solution. The mixture of the red blood cells, white blood cells, sedimenting agent and salt solution was allowed to stand until the red blood cells sedimented to the bottom of the container in which the mixture was placed. The red cells were then separated from the solution, and the white cells were separated from the supernatant and were thereafter transfused into a patient. The red cells and previously withdrawn plasma were then reinjected into the donor. The process was repeated as many times as desired, and usually six times.

The method and apparatus of the instant invention provide a number of advantages over the process disclosed and claimed in my aforementioned U.S. Application Ser. No. 783,380. In one aspect of the instant invention, the withdrawn blood is passed directly to an interrupted flow centrifuge, which is used to separate the red and white cells from the plasma and platelets. In my prior process, the withdrawn whole blood was placed in a flexible bag, which in turn had to be placed in a centrifuge to separate the platelets and plasma. Utilizing the in-line centrifuge, less handling of the whole blood is required, and the entire process can be carried out in a closed system. Because of this increase in efficiency, there is a saving in time of about 30%. Thus, in a given period of time, more blood can be processed with the consequent recovery of a greater number of leukocytes.

In another aspect of the instant invention, there is provided a bag system for processing the red and white cells, and separating the red cells from the white cells. This bag system is used with the centrifuge process and can be used in the process disclosed and claimed in my prior U.S. Application Ser. No. 783,380. The closed bag system provides for greater sterility since the number of occasions for entering the bags, although steriley, is reduced. This in turn lessens the possibility of contamination of the blood, thereby preventing infection of the donor or the patient.

Furthermore, since there is a closed bag system, less time is lost in making all of the connections which are necessary utilizing the procedure disclosed and claimed in my previous application. Time saving is of the essence in leukopheresis procedures since such savings permit larger yields of cells. Having the preassembled closed bag system, less training is necessary for the operator who will carry out the process, with the result that there is less chance for error.

In yet another aspect of this invention, a method and apparatus are provided for increasing the granulocyte count of the donor prior to the leukopheresis. It is well known that the number of granulocytes a normal human blood donor can donate per unit of time is directly proportional to the number of granulocytes he has in his circulating blood at that time. It is also known that all healthy people have a large reserve of granulocytes stored in their bone marrow and other organs and tissues. These reserves exceed by many times the amount of granulocytes that can be taken out of the system. Any means to make the donor release stored cells in his circulating blood would increase the harvest of the cells during blood donation, regardless of the method used for harvesting the granulocytes.

Known means to induce the donor to release such cells include (a) exercise, (b) administration of endotoxins (bacterial extracts) or (c) administration of epinephrine. The exercise is not practical, while the other two means are potentially dangerous.

In one aspect of this invention, a method and apparatus are provided for increasing the donor's white cell count, or leukocytosis. This aspect of the invention utilizes a nylon or other plastic fiber filter to treat a small portion of blood from the donor, and then return the blood to him, prior to the start of the leukopheresis.

It has been shown that the granulocyte count of humans undergoing filtration leukopheresis has a tendency to increase during the procedure after a short lasting drop. Data showing this phenomenon can be found in "Leucocytes: Separation, Collection and Transfusion" edited by J. M. Goldman and R. M. Lowenthal, Academic Press, New York, New York, Pages 177 to 189 (1975). The exact mechanism responsible for this increase of the donor's white cells count is not known. It is known, however, that some agent is formed in the blood after it contacts certain fibers, which agent, when entering the donor again by returning this blood to him, is responsible for release of granulocytes from the reserve stores in his circulating blood.

Although this result of filtration leukopheresis has been known for some time, prior to the instant invention, no practical use has been made of this knowledge. Applicant is now applying this knowledge to increase granulocyte yield in a gravity leukopheresis process. Applicant's invention is also applicable to increasing granulocyte yield in other leukophereses.

It is accordingly an object of this invention to provide a method and apparatus for carrying out a gravity leukopheresis with an in-line centrifuge.

It is another object of this invention to provide a closed bag system utilizable in a gravity leukopheresis process.

It is a further object of this invention to provide a method and apparatus for increasing granulocyte count in a leukopheresis process.

These and other objects of this invention are accomplished by providing a bag system for gravity leukopheresis comprising a first flexible plastic bag and a second flexible plastic bag, said bags being joined by a flexible plastic transfer tube, with said tube placing the interiors of said bags in fluid communication, said first bag having a second tube secured thereon for introducing red and white cells therein, said first bag having a third tube connected thereto for withdrawing white cells therefrom, and said second bag having a second tube connected thereto for introducing plasma therein and a third tube connected thereto for withdrawing red blood cells and plasma therefrom for reinfusion into a donor.

Other objects and many of the attendant advantages of this invention will be readily appreciated as the same becomes better understood by reference to the following detailed description when considered in connection with the accompanying drawings wherein:

FIG. 3 is a schematic view showing the separation of the platelets and plasma from the red and white cells;

FIG. 4 is a partial elevational view of a sedimenting bag, and showing the sterile ports;

FIG. 5 is a partial exploded perspective view showing the method of exposing the sterile ports;

FIG. 6 is a sectional view of the blood filter used in the processes of this invention; and FIG. 7 is a partial exploded view of a plastic spike used for insertion into a sterile port.

Referring now in greater detail to the various figures of the drawings wherein like reference characters refer to like parts, a first system for carrying out this invention is generally shown at 10 in FIG. 1. The granulocyte stimulation system is shown at 12 in FIG. 1.

Figure 1:
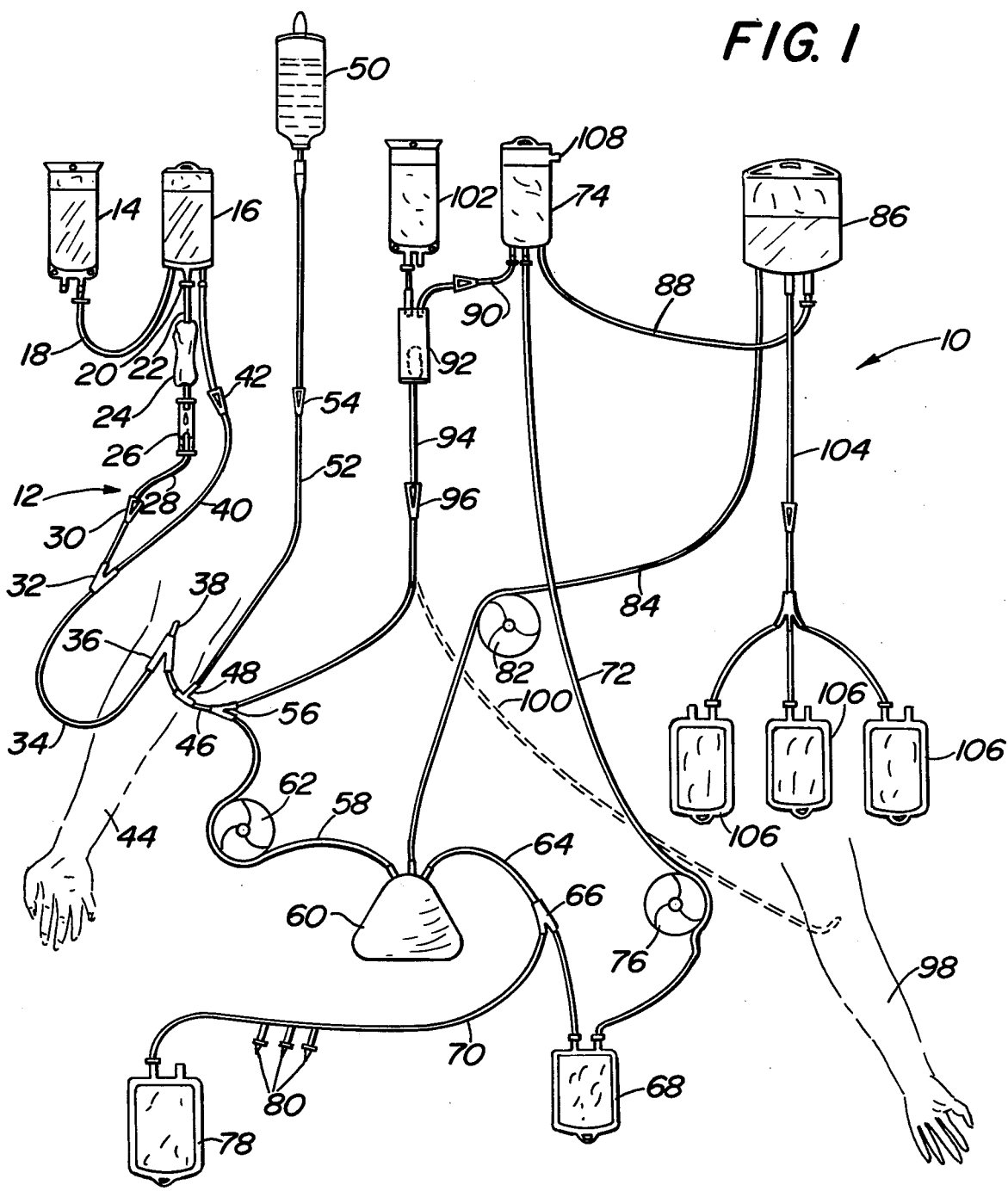
FIG. 1 is a schematic view showing the process of this invention in combination with an in-line centrifuge, and also showing the apparatus for granulocyte stimulation.

Prior to commencing the use of the system for harvesting granulocytes, the granulocyte stimulation system 12 is first used.

The granulocyte stimulation system includes a bag 14 filled with Normal Saline solution (0.9% sodium chloride in distilled water). A second bag 16 contains heparin, in an amount of 200 to 2000 units, depending on how much blood will be used for producing leukocytosis. Bags 14 and 16 are connected by flexible tube 18. Bag 16 is connected, via connector 20 and tube 22, to blood filter 24. Blood filter 24 is a conventional blood filter used in filtration leukopheresis, with the filtering medium comprising nylon fibers.

Blood filter 24 is in turn connected, via suitable flexible tubing, to an infusion chamber 26, the structure of which will be described in greater detail in connection with FIG. 6. The infusion chamber 26 is a standard apparatus which is normally used in filtering blood for any transfusion process. It contains a plastic or metal gauze net, whose purpose is to remove any clots in the blood prior to transfusion.

Chamber 26 is in turn connected to flexible tube 28, which has a suitable clamp 30 thereon. Tube 28 is in turn connected to Y-connector 32. Y-connector 32 is in turn connected to tube 34, which is connected to a second Y-connector 36. Y-connector 36 is in turn connected to a needle or intravenous plastic catheter 38. A plastic tube 40 joins Y-connector 32 with bag 16. A suitable clamp 42 is placed on tube 40.

The process of using system 12 will now be described. Initially, the needle or catheter 38 is inserted in a large vein in the donor's arm 44. The entire system 12 is lowered to be positioned below the arm so that blood can pass from the arm into the system by gravity. The blood, flowing by gravity, passes through lines 34 and 40 into bag 16 containing the heparin. When the appropriate amount of blood is collected, which can vary between 200 and 600 ml, the bleeding is stopped. At this point, the bag 16 is elevated and the line 40 is closed by clamp 42. Tube 22, which has been secured to bag 16 via connector 20, allows the blood and heparin in bag 16 to pass through filter 24 and infusion chamber 26 into line 28. The filtered blood is then returned via line 34 into the arm 44 of the donor.

When all of the blood in bag 16 has passed through the filter 24, the Normal Saline from bag 14 is permitted to enter bag 16 via tube 18. Appropriate clamps are provided wherever necessary to keep the material from one part of the system separate from the remainder of the system until needed. Such a clamp can be used on tube 18 until the Saline from bag 14 is added to bag 16. The Saline then passes from bag 16 through filter 24, infusion chamber 26 and back to the donor. The purpose of the Saline is to displace any blood that may have been retained in the filter 24. However, the Saline will not wash the white cells from the filter in any significant amount.

The exact mechanism by which this process operates is not known, but it is believed that the nylon fibers in filter 24 activate the white blood cells causing some of them to release part of their contents. This activation, coupled with the removal of the white blood cells, even in a small amount, apparently causes the donor to react by increasing the production of granulocytes within his blood by removing the granulocytes from the granulocyte reserve, such as the bone marrow discussed above.

In any event, regardless of the reason that this process causes the granulocyte stimulation, it has been found that within about one hour after the process has been performed, the number of white cells circulating in the donor's blood is substantially increased, in an amount of about 30%. This will in turn increase the number of leukocytes recovered in any given period during which the donor is being acted upon. The entire process of granulocyte stimulation requires only about fifteen minutes. When it is realized that a donor will normally be donating granulocytes over a three to three and one-half hour period, it is seen that the small amount of time spent for the stimulation will result in substantially increased granulocyte yields during the leukopheresis process.

In carrying out the stimulation, as an added precaution, all elements of system 12, including the filter 24, the infusion chamber 26 and all connector tubes can be filled with Normal Saline in order to avoid introducing any air into the donor. After the stimulation process has been completed, the leukopheresis process can commence.

In commencing the leukopheresis process, blood is drawn from arm 44 through catheter 38. The blood passes through the right-hand branch of connector 26 into flexible tube 46. A T-connector 48 is placed in line with tube 46. An anticoagulant, such as ACD (Formula A) is maintained in container 50. The ACD enters the blood line 46 through tube 52, which is connected with connector 48. A suitable clamp 54 can be placed on the ACD line 52.

The blood is mixed with the ACD at a predetermined ratio. Normally, the ratio will be 75 ml ACD per one pint (473 ml) of blood. The blood-ACD mixture then passes through Y-coupling 56 into flexible tube 58. The mixture is then pumped into a centrifuge 60 by a roller pump 62. The roller pump 62 also serves the function of drawing the blood from arm 54 and drawing the ACD from line 52, and maintaining the ratio of blood to ACD.

The centrifuge 60 can be any of the interrupted flow centrifuges normally used in chemical laboratories or in blood banks for carrying out leukophereses. A typical centrifuge which can be used is a Haemonetic centrifuge. The speed of the centrifuge should be such as to spin off the plasma at the top, and leave the platelets, red cells and white cells within the centrifuge. By way of example, when utilizing a 15 cm diameter centrifuge, a speed of approximately 1000 rpm will accomplish this purpose. If desired, after the plasma has been removed from a batch of whole blood, the rotational speed of the centrifuge can be slightly increased to remove the platelets.

The plasma that is spun off by the centrifuge passes through tube 64, through connector 66 and into plasma collection bag 68. A tube 70 is also connected to connector 66. When bag 68 is being filled with plasma, tube 70 is closed, by any suitable clamp.

The plasma in bag 68 is transferred, via tube 72 to bag 74, for subsequent reinfusion, as will be explained hereinafter. A rotary pump 76 propels the plasma to bag 74.

When the red cells, white cells and platelets in the centrifuge 60 reach the middle of the centrifuge bowl, meaning that the entire bowl is now filled with these three components of whole blood, the bleeding is stopped by stopping roller pump 62. At this point, a 3% solution of HES in Normal Saline, which is contained in bag 78, is introduced into centrifuge 60 via tubes 70 and 64. The volume of HES solution in bag 78 can be predetermined, based on the volume of centrifuge 60. Bag 78 also contains a volume of sterile air equal to the volume of centrifuge 60. As will be explained hereinafter, the volume of HES solution should be efficient to achieve an approximate hematocrit of 30%. Line 70 is provided with a plurality of sterile spikes 80 for subsequent insertion into other bags of HES solution for later runs of the process. The sterile spikes are conventional connectors, and the structure of each of them will be described hereinafter in connection with FIG. 7.

As the HES solution is mixed with the red cells, white cells and the platelets in centrifuge 60, the contents of the centrifuge bowl are removed by roller or rotary pump 82 via tube 84. The roller pump 82 can also serve the function of creating a vacuum in a centrifuge in order to draw the HES solution into the centrifuge and mix it with the red cells, white cells and platelets. The pump 82 propels the entire mixture into sedimentation bag 86. The sterile air in bag 78 is allowed to enter centrifuge 60 after all of the HES has been passed through the centrifuge in order to empty the centrifuge completely.

As explained in my aforementioned U.S. Application Ser. No. 783,380, the wider the sedimentation bag, the more quickly separation of red cells and white cells occurs. Accordingly, the width of the bag should be greater than its height. In the bag 86, the red blood cells are permitted to sediment. As explained in my aforementioned U.S. Application Ser. No. 783,380, the HES causes the rapid sedimentation of the red blood cells.

When the red blood cells have sedimented, they are drained from bag 86 via tube 88. Tube 88 is permanently attached to bag 74, and accordingly the red blood cells are drained into this bag by placing bag 86 at a higher level. In bag 74, the red blood cells mix with the plasma which had previously been delivered to the bag via line 72.

The red blood cells and plasma are then returned to the donor's arm 44 through tube 90. Tube 90 enters infusion filter 92, which is identical in structure and function to infusion filter 26. The red cells and plasma then pass through line 80 and connector 56, where they are returned via the catheter 38 to the donor. A suitable clamp 96 can be placed on tube 94.

Alternatively, the red blood cells and plasma can be returned to the other arm 98 of the donor via line 100, which is shown in phantom. When the contents of bag 74 have been returned to the arm 44, or alternatively, while the contents of the bag 74 are being returned to the other arm 98, a new bleeding can be started by reactivating the roller pump 62. The entire process is then repeated.

Whenever there is no bleeding from arm 44, or if there is no return of blood to arm 44 or arm 98, Normal Saline in bag 102 is dripped into the arm via tube 94 or tube 100 in order to keep the catheter in the vein in the arm open.

After all of the red cells in bag 86 have been transferred to bag 74, line 88 is closed by any suitable clamp. At this point, only white cells and the HES-Normal Saline solution remain in bag 86. Additionally, if the platelets were not removed by centrifugation, they will also be present in bag 86. The contents of bag 86 are then drained via tube 104 into one of the empty plastic bags 106. Suitable clamps can be used to insure that only one bag 106 will be filled at any time.

After the contents of bag 86 have drained into one of the bags 106, the filled bag 106 is then disconnected from is associated tube. The bag is then centrifuged at 500 rpm for fifteen minutes. The supernatant HES solution, and platelets, if not previously removed, is then removed from the bag by a bag press, and discarded, leaving the leukocytes in the bag 106. After the entire process has been repeated a number of times, all of the leukocytes in the bags 106 are then pooled into one bag. These leukocytes can then be administered to a leukopenic patient.

As pointed out above, when carrying out the process of FIG. 1, the bags 78, which are secured on spikes 80, and which contain the HES-Normal Saline solution, should also contain a volume of sterile air, which volume is equal to the volume of the centrifuge 60. The purpose of the sterile air is to insure that the entire contents of the centrifuge bowl will be emptied by the roller pump 82 and deposited in bag 86, leaving the centrifuge bowl with only air therein. After the process has been completed, and a new quantity of whole blood is to be processed, and a new bag 78 will be attached to one of the sterile spikes 80.

Bag 74 has a small vent hole at the top thereof. The purpose of the vent hole is to release any air pumped into the bag. The vent hole can be closed with sterile cotton to prevent any contamination with non-sterile air. The vent hole is shown schematically at 108 in FIG. 1.

Figure 2:
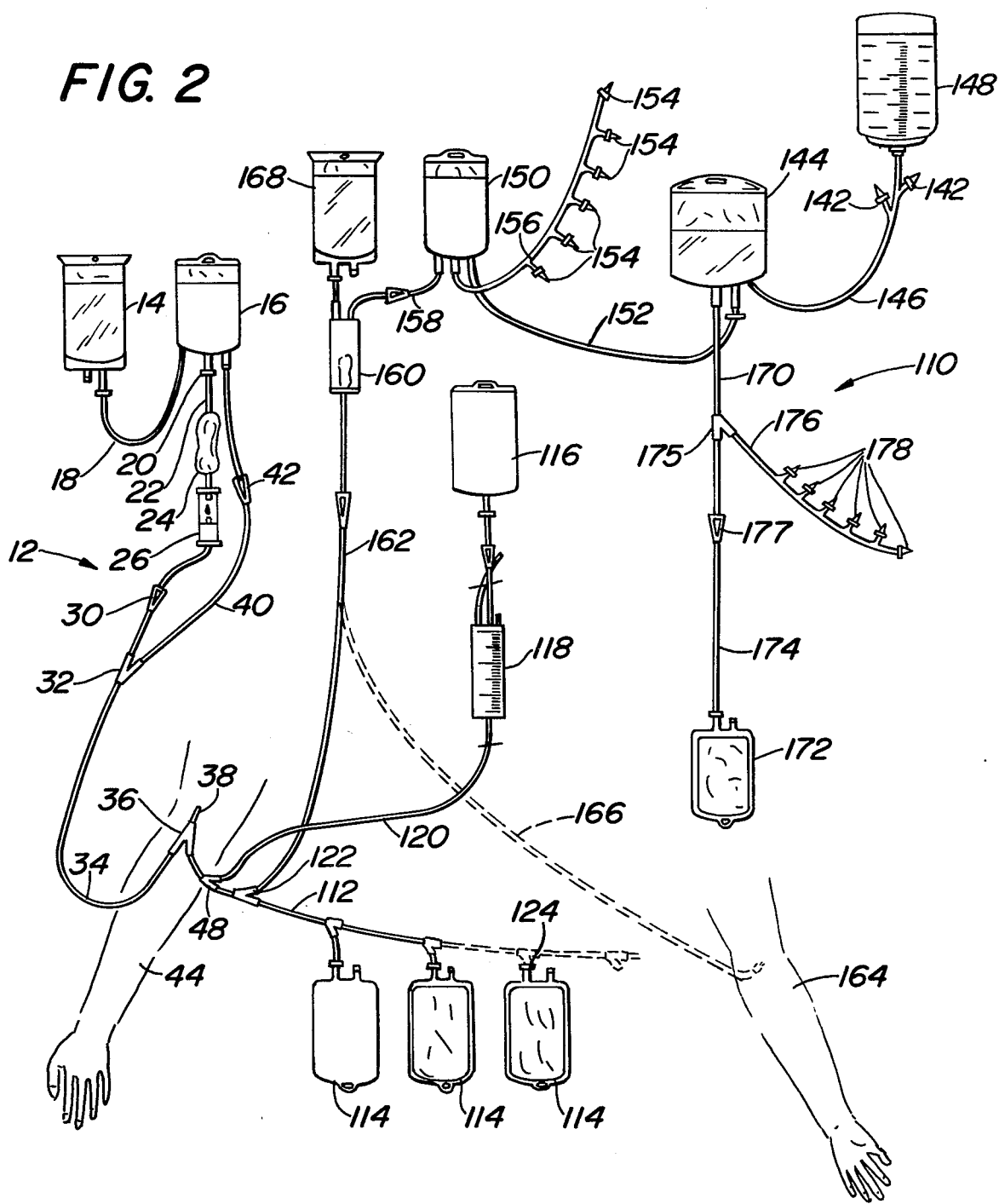
FIG. 2 is a schematic view showing the bag system of this invention for use in gravity leukopheresis, and also showing the system for increasing granulocyte production.

A second embodiment of a process and apparatus for carrying out the leukopheresis of this invention is generally shown at 110 in FIG. 2. The system 110 is quite similar to the system 10 in that it also employs a pair of connector bags for the separation of the red cells from the white cells and for the mixing of the red cells with plasma for reinfusion into the donor. Prior to commencing the leukopheresis utilizing the system 110, the donor can first be stimulated to release additional leukocytes into his blood by utilizing the system 12 used in the process of FIG. 1. The system 12 is identical to that in FIG. 1 and is used in an identical manner.

If the leukocyte stimulation is to be used, after its completion, the leukopheresis is commenced. Initially, blood is passed by gravity flow through tube 112 into a collection bag 114. Each bag has a capacity of 600 ml, and one pint (473 ml) of blood is passed into the bag. Tube 112 has attached thereto as many bags as there are pints (473 ml each) of blood to be processed. Thus, if 6 pints (473 ml each) of blood are to be processed, there will be six bags 114. The entire system is closed so that there can be no contamination.

The blood is channeled through tube 112 to the farthest bag 114 attached to tube 112. Each bag can be prefilled with 75 ml ACD anticoagulant, or alternatively, the anticoagulant can be dripped from container 116 through graduated cylinder 118 and into tube 112 via tube 120 and coupling 122. The anticoagulant solution is mixed immediately with the blood as the blood passes through to tube 112. Thus, a predetermined amount of ACD (60 to 75 ml, and preferably 75 ml) which has already drained from the container into the graduated cylinder 118 will go with the blood entering the first bag 114.

When the bag 114 which is farthest from arm 44 has been filled with one pint (473 ml) of blood, the bag 114 is disconnected from its associated tube 124 by separation between two metal clamps or seals. The bag 114 is centrifuged in a clinical centrifuge to separate the contents thereof into layers comprising red cells, which are lowermost, a buffy coat, which contains the white cells, and the plasma, which is uppermost, and contains the platelets in suspension. The bag is then placed in a bag press 126, with the red blood cells being lowermost. A sterile spike 128, secured on a flexible tube 130, is then inserted in a sterile port in bag 114. Pressure is then brought to bear against the bag 114, and this expulses the uppermost plasma containing the suspended platelets through tube 130, coupling 132, and through tube 134 into collection bag 136. After the plasma has been expressed, plasma bag 136 together with tube 134, Y-coupling 132, tube 138 and bag 140 is disconnected. The plasma and platelets in bag 136 are centrifuged again at higher speed (2800 rpm) or for a longer time (fifteen minutes) to sediment the platelets at the bottom of bag 136. The bag 136 is then placed in the bag press 126 with the platelets being lowermost and the plasma only is expulsed into bag 140 via tube 134, Y-connector 132 and tube 138. The plasma is used for reinfustion into the donor, and the platelets are used for injection into a patient needing platelet transfusion, as set forth in greater detail in my prior U.S. Application Ser. No. 783,380.

After the plasma and platelets have been expressed from bag 114 by bag press 126, the bag 114 is then secured on a sterile spike 142 via a previously unused sterile port on bag 114. The total number of sterile spikes 142 will equal the total number of bags 114 used in the system. The contents of bag 114, which are substantially all red and white cells, are then emptied into large plastic bag 144 via tube 146. Additionally, 500 ml of 3% HES in Normal Saline are added to bag 144 via tube 146 from graduated cylinder 148. Because of the graduations on cylinder 148, the 500 ml of the HES solution can be accurately dispensed. Bag 144, like bag 86 in FIG. 1, has a width which is greater than the height of the bag.

The HES solution and red and white cells in bag 144 are then mixed by shaking the bag 144, and the red cells are permitted to sediment. When they have sedimented, the red cells are transferred from bag 144 to bag 150 via tube 152. The previously removed plasma, which is in bag 136 (FIG. 3), is then introduced into bag 150 by inserting one of the sterile spikes 154 into an unused sterile port of bag 136 and emptying the contents of the bag through tube 156 into bag 150. Here again, there are as many spikes 154 as there are bags 114. Thus, there will be one spike 154 for each pint (473 ml) of blood that is withdrawn during the process.

Once the plasma has been mixed with the red cells in bag 150, the mixture is returned to the donor in the same manner as in the process of FIG. 1. Thus, the mixture will pass from bag 150 through tube 158 and into infusion chamber 160. From chamber 160, the plasma and red cells will be returned to arm 44 via tube 162. Alternatively, the red blood cells and plasma can be returned to the other arm 164 via tube 166, shown in phantom.

The system of FIG. 2 also includes a container of Normal Saline connected to infusion chamber 160. The Normal Saline is to keep the needle or catheter open when no blood is being withdrawn or injected. Here again, suitable clamps can be provided to control the administration of the Normal Saline.

Once the red cells have been removed from container 144, the supernatant white blood cells in HES solution are drained via tube 170 to bag 172 through tube 174 and Y-connector 175. A suitable clamp, similar to clamp 177, keeps tube 170 closed until after the red cells have been drained into bag 150. When the entire remaining contents of bag 144 have been drained, and bag 172 is filled, it is removed from tube 174, sealed and centrifuged in the manner discussed above. The white blood cells are then collected for subsequent injection into a leukopenic patient.

Tube 170 includes a branch tube 176 having a plurality of sterile spikes 178 thereon. Each of the sterile spikes 178 is provided for attachment to a bag 172 for collection of the white blood cells and HES solution from the bag 144. Here again, there will be as many sterile spikes 178 as there are bags 114.

Referring to FIG. 4, there is shown therein a plastic bag 180 having two sterile ports 182 therein. Bags of this type can be used wherever there must be a connection with a sterile spike. The sterile ports 182 are conventional in blood processing bags, and the ports shown herein are solely by way of example. Any of the sterile ports known to this art can be used in carrying out this invention.

Referring to FIG. 5, the sterile port 182 is shown in greater detail. As seen therein, a tube, formed from the same plastic as the plastic of bag 180, is heat sealed into the top of bag 180 along a heat sealed band 184. The tube 186 is thus in fluid communication with the interior of the bag.

Surrounding the tube 186 are a pair of strips 188 of flexible plastic, which can be the same plastic as the plastic from which bag 180 is formed. Normally, the plastic is polyvinyl chloride. Strips 188 are provided with aligned openings 189 for suspending the bag from a hook. A heat sealed line 190 is made in strips 188, thereby joining the strips and leaving a chamber 192 around tube 186. When it is desired to expose the entrance to tube 186 for the insertion of a sterile spike, the upper portions of strips 188 are grasped and pulled apart, thereby breaking the seal 190 (FIG. 5). Ribs 194 are molded into strip 188 to aid in grasping the same.

When the strips 188 are pulled apart, the chamber 192 and the top of tube 186 are exposed. At this point, a sterile spike can be inserted in tube 186 to permit a fluid to enter the bag 180 or to withdraw the fluid from bag 180. The sterile port 182 is used throughout the systems of FIGS. 1 and 2 wherever a sterile port is required.

Referring again to FIG. 4, it is seen therein that after a tube 186 projecting from bag 180 has been exposed, the opening is sealed by bending the tube back on itself and attaching a stainless steel resilient clip 198. This maintains a sterile seal on the bag 180.

An infusion chamber usable in carrying out this invention is generally shown at 200 in FIG. 6. Infusion chamber 200 is identical in structure and function to infusion chambers 26, 92 and 160 discussed above. The chamber is formed from plastic and includes a transparent cylinder 202. It is sealed at the top by a cap 204 and at the bottom by cap 206. A cylindrical screen 208 is placed within the cylinder 202. A fluid-tight plastic ring is formed at the top of screen 208 and is contiguous with the inner wall of cylinder 202. A second ring 212, having an impervious bottom, is secured on the bottom of cylinder 208. Ring 212 is spaced from the inner wall of cylinder 202 by four equally spaced nibs 214. Where the screen 208 is formed from a flexible plastic, it is maintained in the cylindrical form by two vertically extending ribs 216 (one shown in FIG. 6).

A plastic spike 218 is integrally molded with cap 204. A slidable cylindrical cover 220 is removably positioned on spike 218. A nipple 222 is integrally molded with lower cap 206, and it has a flexible tube 224 secured thereon. Tube 224 is provided at its other end with a sterile connector (not shown).

The infusion chamber 200 is used by removing cap 220 and inserting spike 218 into a flexible tube. Fluid, such as blood, enters chamber 200 through spike 218. The blood then passes into cylindrical screen 208 and passes out through the sides thereof. It passes downwardly around nibs 214 and out through nipple 222. The mesh of the screen 208 is sufficiently fine as to trap any blood clots and prevent them from being injected into the donor.

Infusion chambers, such as chamber 200, are standard pieces of equipment for use in leukophereses. Chamber 200 has been illustrated solely for the purpose of example.

A sterile spike utilizable in carrying out this invention is generally shown at 226 in FIG. 7. Spike 226 basically comprises a rigid plastic tube 228, having a tapered end for ease of insertion into a sterile port, and a removable cylindrical plastic cover 230. The tube 228 is supported by a plastic collar 232 which extends from a hollow cylinder 234. Cylinder 234 can be secured to any flexible tube, in a manner well known to the art.

The sterile spike 226 is exemplary of all of the sterile spikes used in carrying out this invention. It is also exemplary of many of the sterile spikes known to the art.

The specific structures of the sterile ports, sterile spikes and infusion chambers form no part of this invention. The devices shown in FIGS. 4 to 7 are solely by way of example. Any similar devices known to the art can be used in carrying out this invention.

As pointed out in my previous U.S. Application Ser. No. 783,380, the greater the width of the sedimentation bag, the more quickly sedimentation is completed. For this reason, bags 86 or 144 are as wide as possible, and have a width which is greater than their height. Preferably, the bags 86 and 144 should have a width greater than 8 inches (20.3 cm). It has been found that when the sedimentation bag has a width of 10½ inches (26.7 cm), the red cells taken from one pint (473 ml) of whole blood and suspended in 500 ml of 3% HES in Normal Saline, the time required for sedimentation can be as short as nine minutes.

It has also been found, as set forth in my prior U.S. Application Ser. No. 783,380, that excellent results are obtained using an HES concentration in the Normal Saline ranging between 1½% and 6%, with the optimum percentage being 3% at a hematocrit of 30%.

Although HES is the preferred sedimenting agent, other red blood cell sedimenting agents or plasma expanders, such as dextran, polyvinylpyrrolidone or fibrinogen can be used in carrying out this invention. Although Normal Saline has been disclosed as a diluent for the HES, it should be understood that other isotonic balanced salt solutions, which may be buffered, can be used in place of Normal Saline. Among the other solutions that can be used are Ringer's solution or Ringer's lactate solution.

The collected granulocytes produced by the method and apparatus of this invention are normally injected in the patient within twenty-four hours after their production, in the same manner as is done in connection with the recovery of granulocytes through the centrifugation or filtration leukophereses presently being carried out.

Insofar as the ratio of HES solution or other sedimenting agent solution to the red blood cells is concerned, the best results have been obtained by utilizing a hematocrit of approximately 30%. However, good results can be obtained by having the hematocrit vary from 25% to 40%.

The capacities of the plastic bags and graduated cylinders used in carrying out the invention can vary to suit the needs of any given leukopheresis. By way of example, the sedimenting bags 86 and 144 should have a capacity of 2000 ml. The graduated cylinder 148 containing the HES solution should have a capacity of at least 1000 ml, or should be larger where greater quantities of blood cells are to be processed. The red blood cell sedimenting bags 86 and 144 should have a sufficient width to create a liquid column of 1 to 4 inches (2.54 to 10.6 cm) when 500 to 800 ml of liquid are placed in them.

The use of the granulocyte stimulation system 12 is optional. However, it does provide an excellent method of stimulating granulocyte production, which results in increased yields of granulocytes after the leukopheresis has been commenced. It has the advantage of being an integral part of the entire leukopheresis process. After the stimulation has been completed, which takes about fifteen minutes, the system 12 is disconnected, and the leukopheresis can commence. Within approximately one hour after the stimulation technique has been performed, the number of white cells being produced by the donor is substantially incresed, in an amount of about 30%.

The in-line centrifugation gravity leukopheresis, shown in FIG. 1, possesses a number of advantages over the process disclosed and claimed in my co-pending U.S. Application Ser. No. 783,380. There is a major saving in labor and time in that the operator need not remove the bag containing the whole blood and place it in a separate centrifuge, and then separately express or aspirate the plasma and platelets from the red and white cells. The entire operation can be carried out at one site within reach of the operator. In view of the increased efficiency, and consequent saving in labor, there is a saving in time of about 30%. Thus, in a given period of time, more blood can be processed with the consequent recovery of a greater number of leukocytes. Alternatively, the same amount of blood can be processed in a shorter period of time, as compared with the process disclosed and claimed in U.S. Application Ser. No. 783,380.

Insofar as the process of FIG. 2 is concerned, here too there are advantages over my prior process. The major advantage is that every time blood is collected from, transferred or returned to the donor, new sterile ports and spikes or preattached connectors are used. In the prior process, the ports were being re-used. Utilizing the new sterile ports and preattached connectors, there is less chance of contamination or infection.

Another advantage of the process of FIG. 2 is that the red cells are removed from an otherwise closed system only once. In my prior process there was no preclosed system. Having only the single removal again presents less possibility for infection to the donor, or via the product, to the patient.

Another advantage is the re-use of bags 144 and 150. In the prior process, the equivalent bags had to be changed with each removal of a pint (473 ml) of blood. Having the present system lowers the cost of the system. Another advantage is the fact that because there is a pre-assembled system, less time is lost in making all of the connections during the procedure, which time was necessary in the previous system. A further advantage is that having the system pre-assembled standardizes the procedure, and less training is needed for the operator, with less chance for error.

It should also be noted that portions of the systems of FIGS. 1 and 2 are identical. Thus, the sedimentation bag, mixing bag, infusion filter and Saline containers are substantially identical in both processes. Accordingly, the equivalent structures are bags 86 and 144, bags 74 and 150, infusion filters 92 and 160 and Saline containers 102 and 168. There are also similar tube connections between the various bags. To this extent, both systems enjoy similar advantages, as described above with respect to the system of FIG. 2.

Without further elaboration, the foregoing will so fully illustrate my invention, that others may, by applying current or future knowledge, readily adapt the same for use under various conditions of service.

What is claimed as the invention is:

1. An apparatus for performing a leukopheresis comprising an interrupted flow centrifuge, means for delivering blood from a donor to said centrifuge, means for withdrawing plasma from said blood in said centrifuge, a first flexible plastic bag, tube means connected with said centrifuge for delivering blood, after the plasma has been removed, from said centrifuge to said plastic bag, a second flexible plastic bag, said first and second flexible plastic bags being joined by a flexible transfer tube, third tube means associated with said first plastic bag, said third tube means being adapted to withdraw white blood cells from said first flexible plastic bag, second tube means secured to said second flexible plastic bag, said second tube means being adpated to introduce the plasma previously removed from the blood into said second flexible plastic bag, and third tube means secured to said second flexible plastic bag, said third tube means being adapted to withdraw red blood cells and plasma from said second flexible plastic bag for reinfusion into a donor.

2. The apparatus of claim 1 and further including means for introducing a red blood cell sedimenting agent into said first flexible plastic bag.

3. The apparatus of claim 2 wherein said introducing means comprises a tube in fluid communication with said centrifuge, whereby said red blood cell sedimenting agent can be introduced into said centrifuge after the plasma has been removed from the blood, and the remainder of the blood can be transferred to said first flexible plastic bag along with said red blood cell sedimenting agent through said tube means connecting said centrifuge with said first flexible plastic bag.

4. The apparatus of claim 3 wherein said introducing tube has a plurality of sterile spikes thereon, with each of said spikes being adapted to be inserted into a sterile port of a bag containing the red blood cell sedimenting agent.

5. The apparatus of claim 1 wherein said third tube means on said second flexible plastic bag is in fluid communication with an infusion filter.

6. The apparatus of claim 1 wherein said means for delivering blood comprises a tube, said delivering tube having one end in fluid communication with said centrifuge and the other end in fluid communication with an intravenous catheter adapted to be inserted in the arm of the donor.

7. The apparatus of claim 1 and further including pump means for delivering the blood from said centrifuge to said first flexible plastic bag.

8. The apparatus of claim 1 and further including pump means for delivering said plasma to said second flexible plastic bag.

9. The apparatus of claim 1 wherein said means for delivering blood from said donor to said centrifuge comprises a tube, and further including pump means associated with said delivering tube for aiding the transfer of the blood from the donor to the centrifuge.

* * * * *